(12) United States Patent
Grothe, Jr. et al.

(10) Patent No.: US 9,720,001 B2
(45) Date of Patent: Aug. 1, 2017

(54) METHODS FOR MASS SPECTROMETRIC BIOPOLYMER ANALYSIS USING OPTIMIZED WEIGHTED OLIGOMER SCHEDULING

(71) Applicant: Thermo Finnigan LLC, San Jose, CA (US)

(72) Inventors: Robert A. Grothe, Jr., Campbell, CA (US); Iman Mohtashemi, Mountain House, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 266 days.

(21) Appl. No.: 14/283,582

(22) Filed: May 21, 2014

(65) Prior Publication Data

US 2015/0338418 A1 Nov. 26, 2015

(51) Int. Cl.
 *G01N 33/68* (2006.01)
 *G06F 19/10* (2011.01)
(52) U.S. Cl.
 CPC ......... *G01N 33/6848* (2013.01); *G06F 19/10* (2013.01)
(58) Field of Classification Search
 CPC ...................................................... G01N 33/68
 USPC ............................................. 436/86–87, 173
 See application file for complete search history.

(56) References Cited

U.S. PATENT DOCUMENTS

| 5,885,841 | A  | * | 3/1999  | Higgs, Jr. ................. C07K 1/12 |
|           |    |   |         | 436/86                                 |
| 7,136,759 | B2 | * | 11/2006 | Kangas .............. G01N 30/8693      |
|           |    |   |         | 530/417                                |
| 7,329,353 | B2 | * | 2/2008  | Dillon .................... C07K 1/023  |
|           |    |   |         | 210/198.2                              |
| 7,409,296 | B2 | * | 8/2008  | Colinge ............. G01N 33/6818      |
|           |    |   |         | 435/4                                  |

(Continued)

FOREIGN PATENT DOCUMENTS

| CN | 103439441 A | 12/2013 |
| WO | WO 2004/013635 A2 | 2/2004 |

OTHER PUBLICATIONS

Smith, C. A. et al, Analytical CHemistry 2006, 78, 779-787.*

(Continued)

*Primary Examiner* — Arlen Soderquist
(74) *Attorney, Agent, or Firm* — Thomas F. Cooney

(57) ABSTRACT

A method for detecting a list of known biopolymer molecules comprises: calculating, for each biopolymer, a respective list of oligomer molecules predicted to be produced by chemical processing; calculating, for each oligomer molecule, a respective predicted chromatographic elution time period; assigning, for each biopolymer molecule, one or more selected oligomer molecules to be detected, wherein the selecting is performed using weighted selection probabilities determined from the predicted elution times; scheduling a plurality of oligomer detection events of a detection system, wherein each oligomer detection event corresponds to a respective one of the predicted elution time (Continued)

periods; performing the chemical reaction or processing of the sample to generate a processed sample; introducing the processed sample into a chromatographic system; introducing any eluting oligomers into the detection system; and operating the detection system so as to search for each of the selected oligomer molecules in accordance with the scheduled detection events.

19 Claims, 8 Drawing Sheets

(56) References Cited

U.S. PATENT DOCUMENTS

| | | | | |
|---|---|---|---|---|
| 7,756,646 | B2* | 7/2010 | Kangas | G01N 33/6848 530/417 |
| 7,851,742 | B2* | 12/2010 | Geromanos | G01N 33/6848 250/281 |
| 7,910,372 | B2* | 3/2011 | Ishihama | G01N 33/6803 436/86 |
| 8,165,820 | B2* | 4/2012 | Gorenstein | G01N 30/72 250/282 |
| 8,187,893 | B2* | 5/2012 | Hunter | G01N 33/6848 436/173 |
| 8,271,203 | B2* | 9/2012 | Hunter | H01J 49/004 250/282 |
| 8,501,487 | B2* | 8/2013 | Krokhin | C07K 7/06 436/86 |
| 8,502,137 | B2* | 8/2013 | Grothe | H01J 49/0036 250/282 |
| 8,658,355 | B2* | 2/2014 | Heaven | G01N 30/7233 250/282 |
| 8,933,396 | B2* | 1/2015 | Louette | B82Y 15/00 250/282 |
| 8,935,101 | B2* | 1/2015 | Wright | G01N 30/8675 250/281 |
| 9,040,903 | B2* | 5/2015 | Coon | G06F 19/18 250/281 |
| 2004/0108452 | A1* | 6/2004 | Graber | G01N 33/6803 250/281 |
| 2004/0121487 | A1* | 6/2004 | Kangas | G01N 30/8693 436/514 |
| 2004/0143402 | A1* | 7/2004 | Colinge | G01N 33/6818 702/19 |
| 2005/0092910 | A1* | 5/2005 | Geromanos | C12Q 1/6872 250/282 |
| 2006/0287834 | A1* | 12/2006 | Kearney | G01N 30/7233 702/27 |
| 2007/0233394 | A1* | 10/2007 | Kangas | G01N 33/6848 702/19 |
| 2008/0021687 | A1* | 1/2008 | Hunter | H01J 49/004 703/11 |
| 2008/0070314 | A1* | 3/2008 | Geromanos | G01N 33/6848 436/86 |
| 2009/0203068 | A1 | 8/2009 | Lopez-Ferrer | |
| 2009/0256068 | A1* | 10/2009 | Petritis | C07K 1/16 250/282 |
| 2009/0269732 | A1 | 10/2009 | Ivey et al. | |
| 2010/0161530 | A1* | 6/2010 | Petritis | G01N 30/8693 706/13 |
| 2010/0288918 | A1* | 11/2010 | Satulovsky | H01J 49/0036 250/282 |
| 2011/0245461 | A1* | 10/2011 | Krokhin | C07K 1/20 530/344 |
| 2011/0288779 | A1* | 11/2011 | Satulovsky | H01J 49/0031 702/19 |
| 2012/0049058 | A1* | 3/2012 | Grothe, Jr. | H01J 49/0036 250/282 |
| 2012/0179389 | A1 | 7/2012 | Reisfeld et al. | |
| 2012/0191685 | A1* | 7/2012 | Albar Ramirez | G01N 33/6848 707/706 |
| 2012/0245857 | A1* | 9/2012 | Lee | G06F 19/00 702/22 |
| 2012/0261568 | A1* | 10/2012 | Coon | G06F 19/18 250/282 |
| 2013/0013273 | A1* | 1/2013 | Grothe, Jr. | H01J 49/0036 703/2 |
| 2013/0068943 | A1* | 3/2013 | Heaven | G01N 30/7233 250/282 |
| 2013/0090862 | A1* | 4/2013 | Krokhin | G01N 30/7233 702/21 |
| 2013/0105684 | A1* | 5/2013 | Louette | B82Y 15/00 250/282 |
| 2013/0210051 | A1* | 8/2013 | Louette | B82Y 15/00 435/23 |
| 2013/0288230 | A1 | 10/2013 | Martynov et al. | |
| 2014/0364337 | A1* | 12/2014 | Hermanson | G01N 33/60 506/12 |

OTHER PUBLICATIONS

Noy, K. et al, Bioinformatics 2007, 23, 2528-2535.*
Pucci, Pucci et al, Rapid Communications in Mass Spectrometry 2007; 21, 3051-3059.*
Stahl-Zeng, J. et al, Molecular & Cellular Proteomics 2007, 6, 1809-1817.*
Renard, B. Y. et al, BMC Bioinformatics 2008, 9, Article 355, 16 pages.*
Lange, V. et al, Molecular Systems Biology 2008, 4, Article 222, 14 pages.*
Schmidt, A. et al, Molecular & Cellular Proteomics 2008, 7, 2138-2150.*
Kuzyk, M. A. et al, Molecular & Cellular Proteomics 2009, 8, 1860-1877.*
Sherman, J. et al, Molecular & Cellular Proteomics 2009, 8, 2051-2062.*
Duncan, M. W. et al, Proteomics 2009, 9, 1124-1127.*
Whiteaker, J. R. et al, Molecular & Cellular Proteomics 2010, 9, 184-196.*
Picotti, P. et al, Nature Methods 2010, 7, 43-48.*
Bertsch, A. et al, Journal of Proteome Research 2010, 9, 2696-2704.*
Hewel, J. A. et al, Molecular & Cellular Proteomics 2010, 9, 2460-2473.*
Kiyonami, R. et a, Molecular & Cellular Proteomics 2011, 10, Article 1074, 11 pages.*
Calvo, E, et al, Expert Review of Proteomics 2011, 8, 165-173.*
Gallien, S. et al, Journal of Mass Spectrometry 2011, 46, 298-312.*
Li-Thiao-Te, S. et al, Journal of Computational Biology 2012, 19, 349-364.*
Boja, E. S. et al, Proteomics 2012, 12, 1093-1110.*
Escher, C. et al, Proteomics 2012, 12, 1111-1121.*
Gallien, S. et al, Proteomics 2012, 12, 1122-1133.*
Gallien, S. et al, Molecular & Cellular Proteomics 2012, 11, 1709-1723.*
Nahnsen, S. et al, BMC Bioinformatics 2012, 13 (Suppl 16), Article 58, 9 pages.*
Hewel, J. A. et al, Journal of Proteomics 2013, 81, 159-172.*
Zerck, A. et al, BMC Bioinformatics 2013, 14, Article 56, 14 pages.*
Jeudy, J. et al, Analytical and Bioanalytical Chemistry 2014, 406, 1193-1200.*
Brusniak, M.-Y. et al, BMC Bioinformatics 2008, 9, Article 542, 22 pages.*
Sherwood, C. A. et al, Journal of Proteome Research 2009, 8, 4396-4405.*
Schmidt, A. et al, Current Opinion in Chemical Biology 2009, 13, 510-517.*
Domon, B. et al, Nature Biotechnology 2010, 28, 710-721.*
Li, Y. F. et al, Journal of Proteome Research 2010, 9, 6288-6297.*
Geromanos, S. J. et al, Proteomics 2011, 11, 1189-1211 and supporting information.*
Savitski, M. M. et al, Analytical Chemistry 2011, 83, 8959-8967.*
Moruz, L. et al, Proteomics 2012, 12, 1151-1159.*

(56) References Cited

OTHER PUBLICATIONS

Bailey, D. J. et al, Proceedings of the National Academy of Sciences 2012, 109, 8411-8416.*
Rost, H. et al, Molecular & Cellular Proteomics 2012, 11, 540-549.*
Krokhin, "Sequence-Specific Retention Calculator. Algorithm for Peptide Retention Prediction in Ion-Pair RP-HPLC: Application to 300- and 100-A Pore Size C18 Sorbents", Analytical Chemistry 2006, vol. 78 (22), pp. 7785-7795.
Sun, et al., "BPDA2d-a 2D global optimization-based Bayesian peptide detection algorithm for liquid chromatograph-mass spectrometry", Bioinformatics 2011, vol. 28 (4), pp. 564-572.
Uglea, "Liquid Chromatography of Oligomers", ISBN: 0-8247-9720-5, 1996, Chpt. 3, pp. 42-82.
Shao et al., "Application of peptide retention time in proteome research", Chinese Journal of Chromatography, 2010, vol. 28 (2), pp. 128-134.

* cited by examiner

METHODS FOR MASS SPECTROMETRIC BIOPOLYMER ANALYSIS USING OPTIMIZED WEIGHTED OLIGOMER SCHEDULING

FIELD OF THE INVENTION

The present invention relates generally to mass spectrometry, and more particularly to methods of characterizing a plurality of biopolymer analytes in a biological sample by mass spectrometric detection of oligomer molecules formed by fragmentation, cleavage or digestion of the various biopolymers.

BACKGROUND OF THE INVENTION

Mass spectrometry has advanced over the last few decades to the point where it is one of the most broadly applicable analytical tools for detection and characterization of a wide class of molecules. Mass spectrometric analysis is applicable to almost any species capable of forming an ion in the gas phase, and, therefore, provides perhaps the most universally applicable method of quantitative analysis. In addition, mass spectrometry is a highly selective technique especially well suited for the analysis of complex mixtures of different compounds in varying concentrations. Mass spectrometric methods provide very high detection sensitivities, approaching tenths of parts per trillion for some species. As a result of these beneficial attributes, a great deal of attention has been directed over the last several decades at developing mass spectrometric methods for analyzing complex mixtures of biomolecules, such as peptides, proteins, carbohydrates and oligonucleotides and complexes of these molecules.

One common type of application of mass spectrometry to analysis of natural samples involves the characterization and/or quantification of components of complex mixtures of biomolecules. Many such biological molecules of interest are biopolymers, such as polynucleotides (RNA and DNA) polypeptides and polysaccharides. Generally, the chemical composition (related to the specific collection of monomers of which the polymer is comprised) and the sequence of monomers are the distinguishing analytical characteristics of biopolymer molecules of a given class. However, since biopolymer molecules of a given class generally have high molecular weights and can generate ions having a wide range of charge states, distinguishing various molecules within a mixture of such molecules by mass spectrometry can be challenging.

One important application of mass spectrometry analysis of biopolymers occurs in the field of protein studies (proteomics). In such studies, two types of protein sequencing methods have become popular: (1) the so-called "bottom-up" approach and (2) the so-called "top-down" approach. In the top-down method intact proteins are ionized and directly sampled by the mass spectrometer and then fragmented during MS/MS analysis. Performing mass spectrometric analyses using such an approach can be challenging for the reasons stated above. In the alternative bottom-up approach, a protein-containing sample is digested with a proteolytic enzyme resulting in a complex mixture of peptides, which may be considered to be oligomers. Next, the digested sample is chromatographically separated (in one or multiple dimensions) such that the digest components elute at various times according to their column retention times (RTs). The various eluting components are then introduced to an ion source, usually an electrospray ionization (ESI) source, on a mass spectrometer. The ESI source converts condensed phase ions, eluting from the HPLC column, to multiply-protonated molecules (cations) in the gas-phase. The mass spectrometer then detects the ions and identifies the various peptides using, generally, the technique of tandem mass spectrometry, which is sometimes referred to as "MS/MS" spectrometry or "selected-reaction monitoring" (SRM) and is discussed in greater detail below. In a typical "shotgun proteomics" experiment a cell lysate or other sample, containing as many as several thousand proteins, is analyzed using the bottom-up approach.

During tandem mass spectrometry operation, various precursor ion types that have been chosen to represent respective peptides are isolated. The isolated precursor ions are then subjected to fragmentation (e.g., in a collision cell), and the resulting fragment (product) ions are transported for analysis in a second stage of mass analysis or a second mass analyzer. The method can be extended to provide fragmentation of a selected fragment, and so on, with analysis of the resulting fragments for each generation. This is typically referred to an $MS^n$ spectrometry, with n indicating the number of steps of mass analysis and the number of generations of ions. Accordingly, $MS^2$ mass analysis (also known as an MS/MS mass analysis) corresponds to two stages of mass analysis with two generations of ions analyzed (precursor and products). A resulting product spectrum exhibits a set of fragmentation peaks (a fragment set) which, in many instances, may be used as a fingerprint to identify the peptide from which the particular precursor and product ions were derived.

Although a single SRM transition can be used to successfully identify a particular peptide, in order to identify each of the various proteins from which the peptides were formed (during the digestion step), generally more than one diagnostic peptide is required. In particular, a certain number, Q, of peptide identifications is considered to be necessary in order to confidently infer the presence of a particular protein in the original sample the possibility exists that any given peptide may be generated in the digest from more than one protein. Using more than one peptide of the digest as a marker for a given protein provides redundancy in case the same identical peptide should, by chance, be formed in the trypsin digestion of more than one protein. Conventionally, three peptides are considered adequate to infer the presence of a particular protein (that is, Q=3).

Because the various peptides generated in a tryptic digest will elute at various times during bottom-up proteomics experiments, the mass spectrometer system should be programmed so as to search for the various diagnostic ions at appropriate times during the course of the chromatographic elutions. Unfortunately, however, one often encounters a problem in scheduling SRMs or targeted MS/MS acquisitions based upon the expected retention times. Similar scheduling problems occur, in general, in various situations in which the demand for a resource is not equally distributed over time. Surges in demand create a problem when there is a ceiling on the maximum amount of resource that can be delivered per unit time. A common example of this is power usage in the afternoon on a hot, summer day. In the case of power distribution or in many other cases where consumers pay for a utility or a good, the free market can provide a solution by assigning a higher price to consumption during periods of high demand. This has the effect of encouraging some fraction of price-sensitive users to reschedule their usage to periods of lower demand, thus leveling out the overall demand for the good.

As a general rule, the distribution of retention times is approximately Gaussian, with a peak density in the center and much lower density in the tails. The shape of this distribution is fundamental because the retention time of a peptide can be accurately approximated as the sum of the retention times of its constituent amino acid residues. As a result, the distribution of retention times of randomly generated peptides obeys the Central Limit Theorem of statistics. The Central Limit Theorem states that the sum of independent, identically distributed random variables tends to a Gaussian distribution as the number of terms in the sum increases. Peptides with more than 5 or 6 residues, as are commonly encountered in proteomics experiments, produce retention time distribution that follow the expected Gaussian distribution.

The phenomena which give rise to the SRM scheduling problem discussed above are schematically illustrated in FIGS. 1-2. Curve 10 in the lower portion of FIG. 1 represents a hypothetical chromatogram (detected ion intensity plotted against retention time) showing the elution of numerous peptides—each corresponding to a peak in the chromatogram—during the course of a single experimental run. For illustration purposes only, it is assumed that the chromatogram 10 includes a total of 170 separate elution peaks. For convenience, each peptide may be referred to by a numerical index, k, where 1≤k≤170 and where, in this example, the index k is assigned in order of elution. The elution periods are indicated for a subset of the various peptides by horizontal lines in the upper portion of FIG. 1. For example, the horizontal bar k5 indicates the elution of the fifth peptide (i.e., the peptide for which k=5). Likewise, the horizontal bars k10, k20, k30, k50, k60, k100 and k120 indicate the elution of the peptides for which k=10, k=20, k=30, k=50, k=60, k=100 and k=120, respectively. Note that the index k is plotted along the vertical axis of the upper portion of FIG. 1. The small vertical bars at the end of each horizontal bar indicate the respective elution start and elution end times for the respective peptide. For clarity, the elution periods corresponding to other peptides are not specifically indicated but may be assumed to follow the general trend shown in the upper portion of FIG. 1.

As a general rule, not all of the chromatographic peaks of the chromatogram 10 may be fully resolved because of overlap of some closely spaced peaks. The lower portion of FIG. 1 illustrates that the density of peaks is generally greater in the center of the run because of the adherence to the Central Limit Theorem as noted above. The central region of greater peak density gives rise to greater peak overlap in this region, relative to the beginning and ending portions of the experimental run, as is schematically illustrated in the upper portion of FIG. 1.

FIG. 2A schematically illustrates the expected general form of a histogram of the number of peptide peaks per each segment of the total chromatographic run of a protein tryptic digest, if one were to partition the total run time into equal time segments and count the number of eluting peptide peaks in each segment. For example, the vertical bars centered at retention times $t_1$-$t_{10}$ in FIG. 2A represent the hypothetical distribution of peak counts per partition if one were to partition a chromatogram such as the one illustrated in the bottom portion of FIG. 1A into ten equal-width time segments. According to the Central Limit Theorem analysis, the form of such a histogram should approach the form of a Gaussian probability density distribution, shown as curve 80, as the total number of peptides increases and the partition width decreases. The peptide selection probability density at any time point may be defined as the probability per unit time of selecting a peptide within a time partition that includes the time point. If one were to select peptides to be detected uniformly at random from such a Gaussian distribution, i.e. without taking into account the predicted retention times, the distribution of retention times of the selected peptides would be essentially the same as the underlying distribution, i.e. Gaussian. In this case, one would encounter the disadvantage of having significantly fewer SRMs or MS/MS events per unit time at the beginning and the end of the experimental run and many more in the middle of the run, resulting in a suboptimal, inefficient utilization of the mass analyzer, and possibly in undesirable results. In some cases, this is unavoidable. The inventors have realized, however, that in many other cases, there is freedom in experimental design that allows one to distribute the demand for SRMs or MS/MS events evenly over a chromatographic run.

SUMMARY OF THE INVENTION

A method for detecting, within a sample, the presence or quantity of each of two or more biopolymer molecules of a list of known biopolymer molecules, comprises: calculating, for each biopolymer molecule, a respective list of oligomer molecules predicted to be produced by a chemical reaction or processing of the respective biopolymer molecule; calculating a respective predicted chromatographic elution time period for each oligomer molecule of each list of oligomer molecules; for each biopolymer molecule, assigning one or more oligomer molecules selected from the respective list of oligomer molecules as a proxy for the respective biopolymer molecule, wherein the selecting is performed using a set of weighted selection probabilities that are determined from the predicted chromatographic elution times; scheduling a plurality of oligomer detection events of a detection system, wherein each oligomer detection event corresponds to a respective one of the predicted chromatographic elution time periods of the selected oligomer molecules; performing the chemical reaction or processing of the sample so as to generate a processed sample; introducing the processed sample into a chromatographic system such that oligomers eluting from the chromatographic system, if any, are introduced into the detection system; and operating the detection system so as to search for the presence or quantity of each of the selected oligomer molecules in accordance with the plurality of scheduled oligomer detection events.

According to various embodiments, the assigning of the one or more oligomer molecules may use a set of weighted selection probabilities chosen so as to cause an oligomer selection probability density distribution to be substantially uniform with respect to a retention-time prediction index, such as the well-known hydrophobicity index. According to various embodiments, the assigning of the one or more oligomer molecules may use a set of weighted selection probabilities chosen so as to cause the plurality of scheduled oligomer detection events to be substantially evenly distributed in time. According to various embodiments, the assigning of the one or more oligomer molecules may use a set of weighted selection probabilities chosen such that a number of overlaps of scheduled oligomer detection events is substantially uniform with respect to time. According to various embodiments, the assigning of the one or more oligomer molecules may use a set of weighted selection probabilities chosen such that a selection probability weighting factor progressively increases away from a time at which a maximum number of oligomer molecules co-elute. According to various embodiments, the assigning of the one or more oligomer molecules may use a set of weighted selection probabilities chosen such that a selection probability weighting factor progressively increases away from a mean oligomer molecule elution time.

In various embodiments, the biopolymer molecules are proteins, the oligomer molecules are peptides, the performing of the chemical reaction or processing of the sample comprises performing a tryptic digest the proteins, and the operating of the detection system comprises operating a mass spectrometer detection system, such that specific ions generated from each oligomer molecule may be detected. Accordingly, as one example of the methods of the present teachings, the case of characterizing a list of proteins of interest by the method of bottom-up proteomics is considered. The characterization involves assaying a selected subset of tryptic peptides from these proteins. The sequences of the tryptic peptides can be predicted because the sequences of the proteins of interest are known in advance. This allows prediction of the expected retention times of the peptides in advance using one of a number of available modeling tools. Given this predicted retention-time distribution, a subset of tryptic peptides from the overall pool of tryptic peptides is selected that represents essentially optimal utilization of the analyzer by creating an essentially uniform schedule of SRMs or MS/MS events. According to the methods in accordance with the present teachings, the distribution of scheduled peptide detection events along the time axis is caused to be as evenly distributed as possible over the course of an experimental run.

To accomplish this efficient SRM scheduling, peptide selection is weighted so as to favor those peptides that occur in low-peak-density regions of the retention time histogram over peptides that occur in high-peak-density regions. The probability of selecting a peptide at a particular point in time is equal to the retention time probability distribution (generally a Gaussian distribution as noted above) times a probability weighting factor we are free to choose. The idea of the present teachings is to artificially increase the selection probability of peptides whose elution times (retention times) fall in the tails of the retention time distribution and artificially decrease the selection probability of those peptides that fall in the center of the distribution. Specifically, to cause the scheduling of selected peptides to be as evenly distributed as possible over the entire run time period, we construct a selection process in which the weighting factor for any peptide is exactly reciprocal to the number of other peptides with which its elution time period is overlapping. This choice of weights yields a selection that makes the number of overlapping-in-time peptide elution periods as evenly distributed as possible, statistically speaking, over the entire run.

BRIEF DESCRIPTION OF THE DRAWINGS

The above noted and various other aspects of the present invention will become apparent from the following description which is given by way of example only and with reference to the accompanying drawings, not drawn to scale, in which.

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended figures taken in conjunction with the following description.

Figure 1:
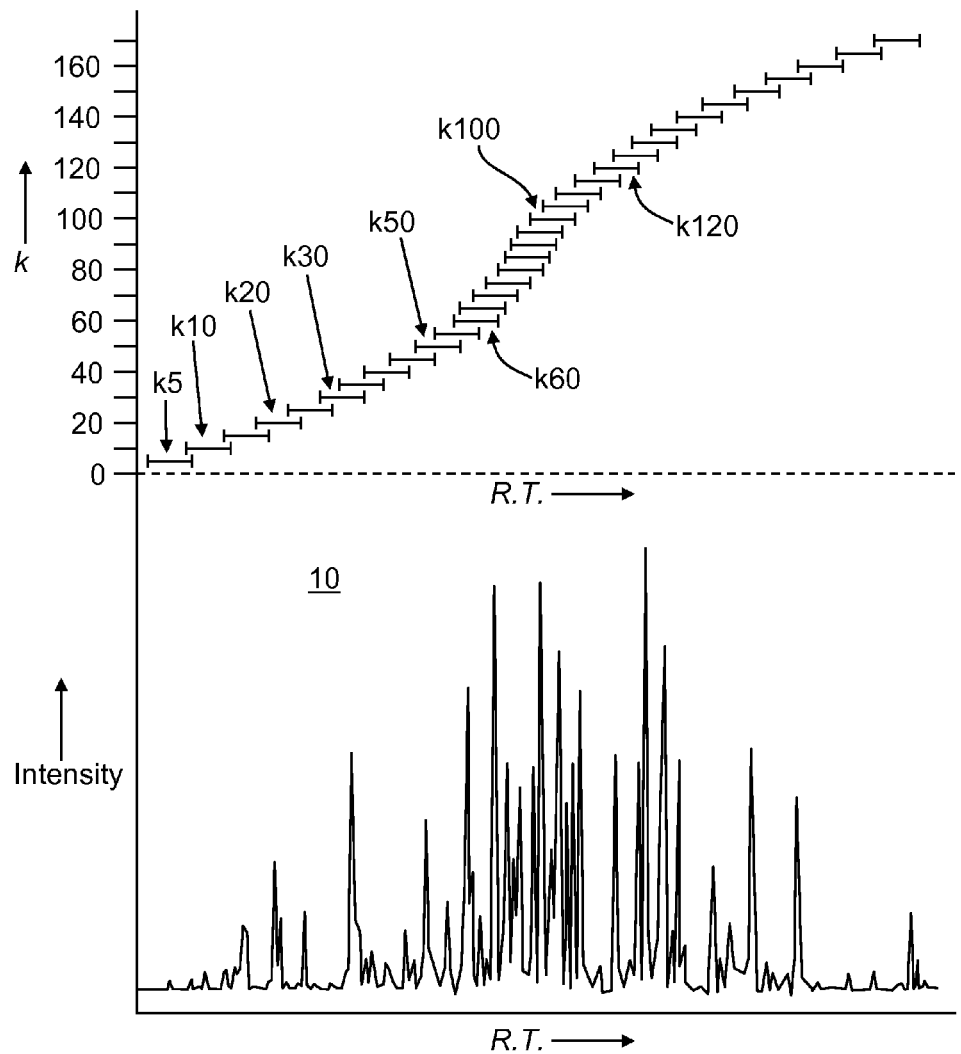
FIG. 1 is a schematic diagram of a hypothetical chromatogram of peptides produced by tryptic digest of one or more proteins (lower portion) and the elution time ranges of the component peptides (upper portion)
Figure 2A:
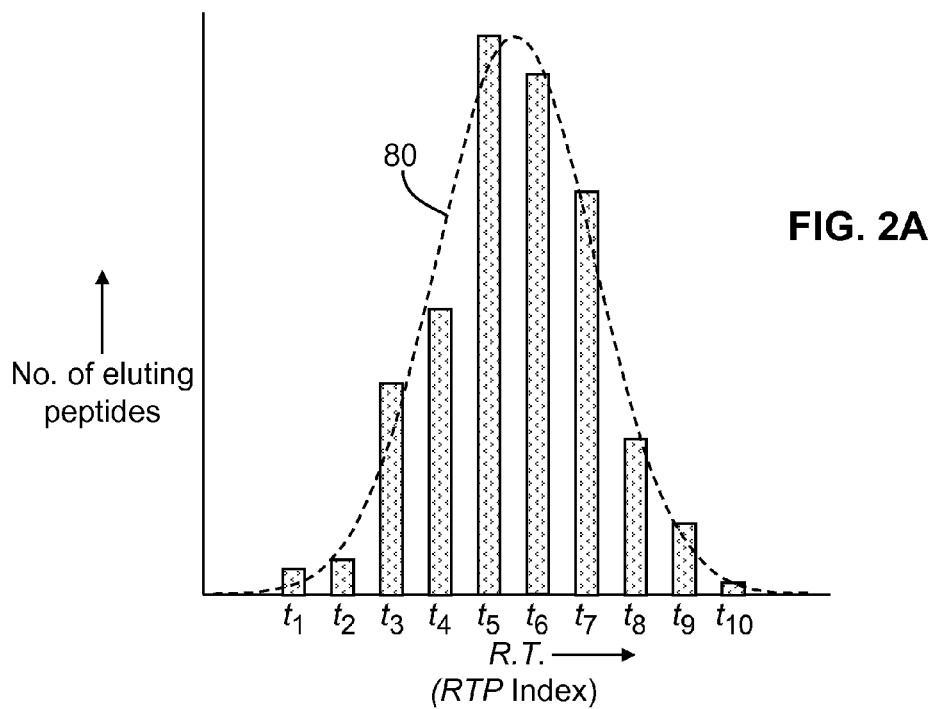
FIG. 2A is a hypothetical expected histrogram of the distribution of peptides expected from a chromatogram of the type shown in FIG. 1.
Figure 2B:
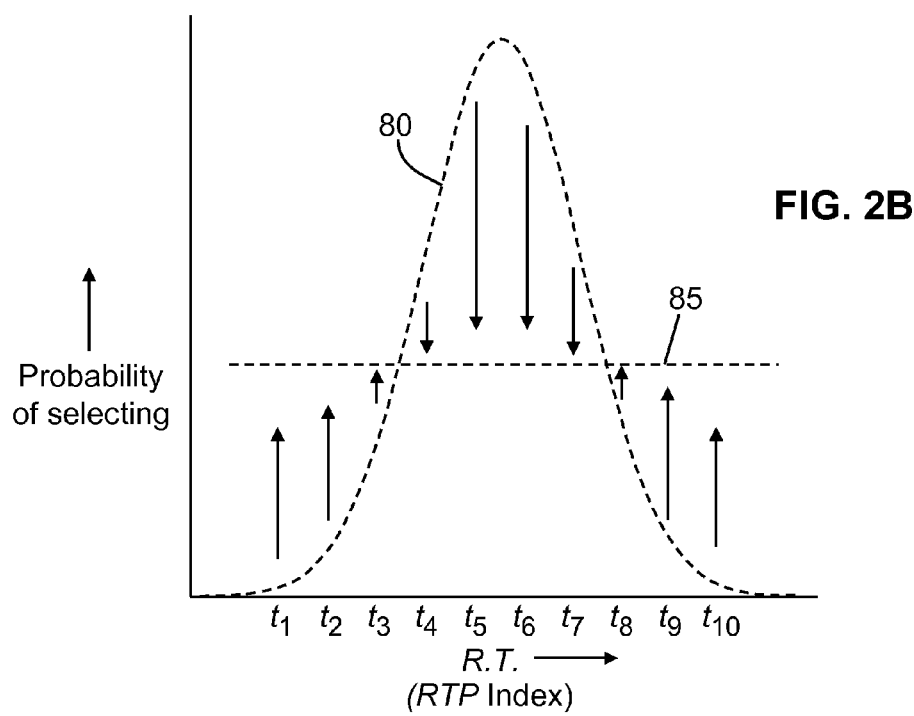
FIG. 2B is an approximate schematic depiction of the way in which peptide selection probabilities may be modified, in accordance with the present teachings, so that scheduled peptide detection events during an experimental run are caused to approach a uniform distribution over time.

FIG. 2B is an approximate schematic depiction of the way in which peptide selection probabilities may be modified, in accordance with the present teachings, so that scheduled peptide detection events during an experimental run are caused to approach a uniform distribution over time. In order to design a "shotgun proteomics" multiple protein assay, one needs to select, for each protein of interest, a group of diagnostic tryptic-digest peptides whose presence will proxy for that of the parent protein. However, as discussed above, if one randomly selects these diagnostic proxy peptides from the natural Gaussian-like distribution of peptides (see FIG. 2A), then problems may occur in the scheduling of peptide detection events, since a large portion of the peptides elute within a narrow time range (relative to the total time range of an experimental run).

As discussed further below, the expected retention times of the various eluting oligomers may be modeled in terms of a retention-time prediction index, such as the so-called hydrophobicity index, which is a quantity derived from chemical composition or other chemical or molecular properties or from experimental parameters. Thus, the retention-time prediction index may be used, e.g., in FIGS. 2A-2B, as a proxy of substitute for actual retention times. Accordingly, the horizontal axis in FIGS. 2A-2B is schematically labeled in terms of both retention time (R.T.) and retention-time prediction index (RTP index). The retention-time prediction index is of use in providing general models of relative elution behavior of different chemical compounds, since actual retention times may depend on particulars of any experimental setup.

Using some analyte detection techniques, such as tandem mass spectrometry, the sequence of operations that needs to be performed for detecting a particular analyte will vary with the nature of the analyte. With other detection techniques, such as UV-visible spectroscopy, vibrational spectroscopy or fluorescence spectroscopy, the near simultaneous occurrence of multiple overlapping elution events may produce a complex signal that is difficult to decompose. Thus, overlapping elution events may cause errors or other difficulties in detection. Accordingly, the inventors have conceptualized methods of calculating a set of probability weighting factors so as to (as indicated by the arrows in FIG. 2B) artificially increase the probability of selecting peptides whose retention times fall in the tails of the natural Gaussian-like distribution and decrease the probability of selecting peptides in the center of the distribution.

One can generalize the probability weighting scheme (or probability density weighting scheme) illustrated in FIG. 2B by recognizing that the probability adjustments can be considered as multiplication of each probability (or probability density) value by a variable multiplicative weighting factor that progressively increases away from the top of the curve 80 (or, as an alternative approximation, away from the maximum or middle value of the histogram). For example, to adjust the values near the top of curve 80 to the level of the uniform distribution line 85, each of the original probability density values is multiplied by weighting factor of approximately 0.58. At the two points where the uniform distribution line 85 crosses the curve 80, the weighting factor has increased to 1.00. Further towards the left and right edges of the diagram, the weighting factor is progressively greater still. This generalization holds regardless of the position of the line 85 relative to the top of curve 80. By implementing such a procedure, the distribution of selected peptides should approach a distribution that is uniform in terms of retention-time prediction index, as represented by the horizontal line 85 in FIG. 2B (see also FIG. 5B).

One possible way of making the distribution of selected peptides flat with respect to time (i.e., like horizontal line 85) might be to simply weight each peptide by the inverse of its probability density that appears on the histogram or on the Gaussian approximation to the histogram and then normalize the so-weighted probabilities between the beginning detection time and the ending detection time of any experimental run. In order to create the probability weighting factors, the identities of the peptides and their various elution times need to known or estimated. This information can be predicted, in many cases, using known tryptic digestion modeling and peptide retention time modeling algorithms as further discussed below with reference to the method 200 illustrated in FIG. 4. Noting that, in the limit of an infinite number of partitions having widths approaching zero, the histogram mode and mean both approach the Gaussian mean, the probability weighting procedure can be simplified by noting the position of either the mode or the mean of the predicted histogram and choosing probability weighting factors that decrease away from this point, either in a time-increasing or time-decreasing direction. The weighting scheme could be based on a chosen functional form—such as a linear function, a polynomial function, a Gaussian-like function or some other form—used to approximate the decrease of weighting factors away from the histogram mode or mean. Then, with this weighting scheme, the probability of populating any given bin of the histogram is uniform, where the "bins" are considered to be a set of equal-time-width segments (partitions) of the total detection time period (the time period during which the detector is operating to detect the peptides).

Although the simple weighting scheme described above is contemplated by and may be included in various methods in accordance with the present teachings, it does not produce optimal scheduling results. Instead, the best procedure is to cause the scheduled peptide-detection events to be as evenly distributed on the time line as possible, where each "scheduled peptide-detection event" comprises a definite time period—having a respective start time and a respective stop time—during which a signature of the respective peptide is to be searched for. This best procedure is slightly different than generating a uniform histogram, because the bins of the histogram are arbitrary, while the detection-event scheduling depends upon the retention times themselves. This procedure of causing the scheduled peptide-detection events to be as evenly distributed as possible also causes the number of overlaps—the occurrence of simultaneous scheduled peptide detection events—to also be as evenly distributed as possible. In other words, although the scheduled detection events of two or more peptides may overlap during an experimental run, there should be no time point during the run at which the number of overlapping detection events is significantly greater than (or less than) the average number of overlaps.

Accordingly, FIG. 4 is a flow diagram of a general method 200 in accordance with the present teachings. According to the method, one starts with a pool of target proteins. This list may comprise a total of M specific proteins of interest, the presence or absence of which one wishes to determine in regard to a sample. Alternatively or additionally, one may wish to determine the concentrations of the various specific proteins in the sample. For each such protein (iterated steps 202-208, FIG. 4A), an ideal (calculated) tryptic digest is determined in silico (step 204) using any one of a number of available chemical digestion simulation models. These model calculations generate a master list of theoretical tryptic peptides (step 206) from each one of the pool of proteins of interest. Optionally (step 210), one can filter the peptide list by restricting it so as to include only prototypic peptides, which are peptides which are most readily detected by a mass spectrometer. Optionally (step 211), one can, either after population of the master peptide list or during its generation, eliminate "degenerate" peptide entries which result from situations in which more than one protein gives rise to the same identical peptide (i.e., same chemical composition and amino acid sequence) during the digestion stage.

After the theoretical tryptic digest has been calculated, a predicted retention time is calculated for each such peptide (step 212). A number of retention time calculation models are available for this purpose. The calculation of retention time may make use of a retention-time predictor index, which may be a quantity that may be calculated from molecular composition, molecular structure or other chemical or molecular properties or some combination of such properties. The retention-time prediction index (RTP index) may also be calculated from parameters related to properties of the type of chromatographic column employed. For example, the semi-empirical metric known as "hydrophobicity index" is one type of retention-time prediction index. A value of the hydrophobicity index may be calculated for each peptide based on the peptide composition. Peptide retention times that are observed in reverse-phase high pressure liquid chromatograph (RP-HPLC) are found to depend on peptide hydrophobicity and can be modeled in terms of the hydrophobicity index.

Figure 3:
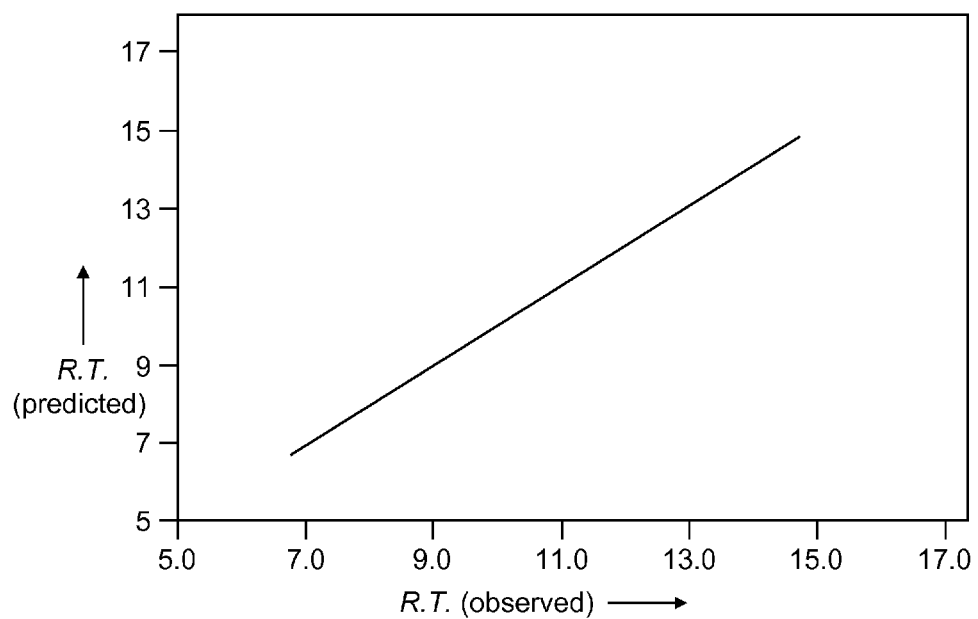
FIG. 3 is a generalized depiction of the manner by which actual peptide retention times may be modeled by using a calibration set that includes peptides covering a range of values of hydrophobicity index.
Figure 4A:
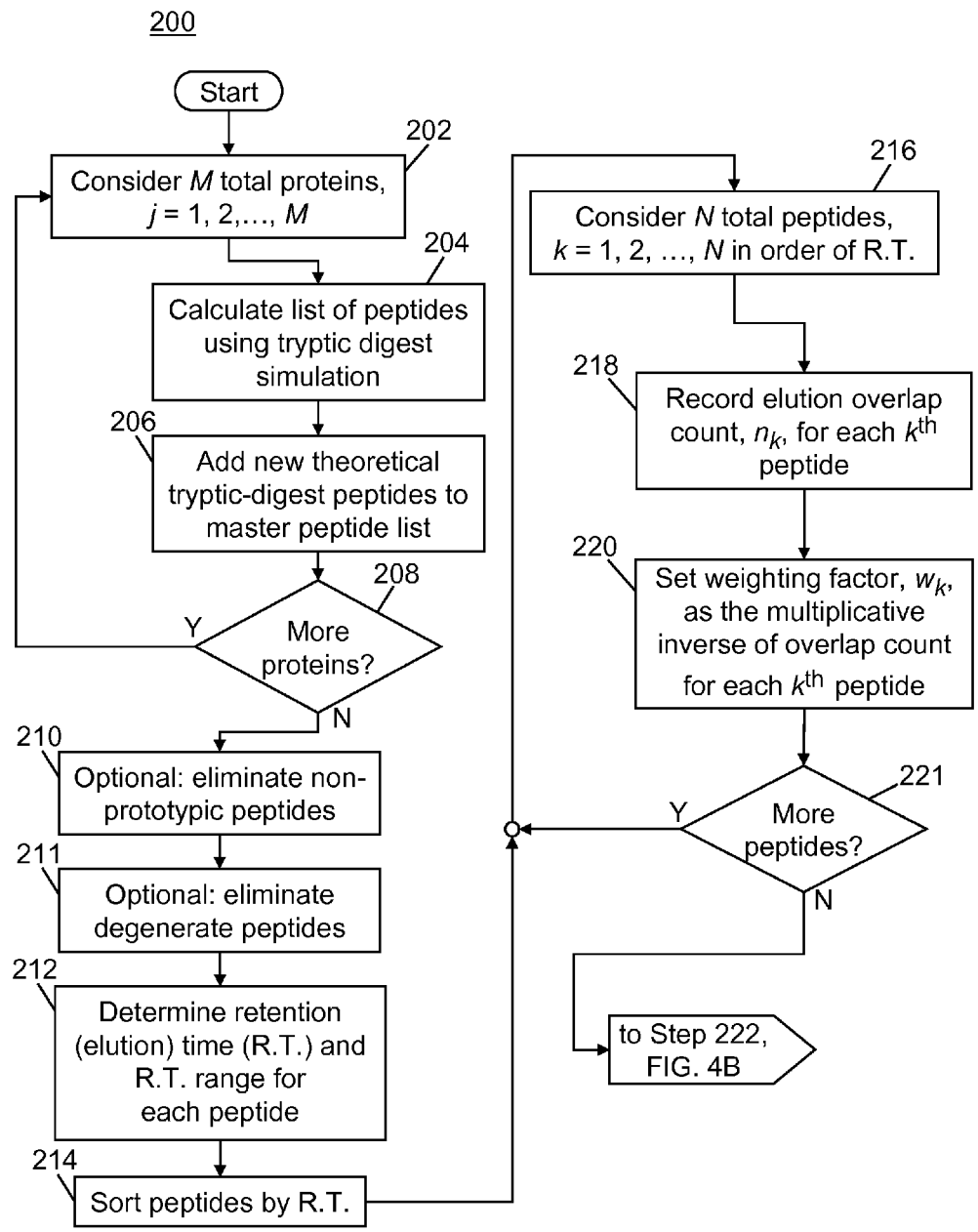
FIGS. 4A-4D depict a flow diagram of a method in accordance with the present teachings.
Figure 4B:
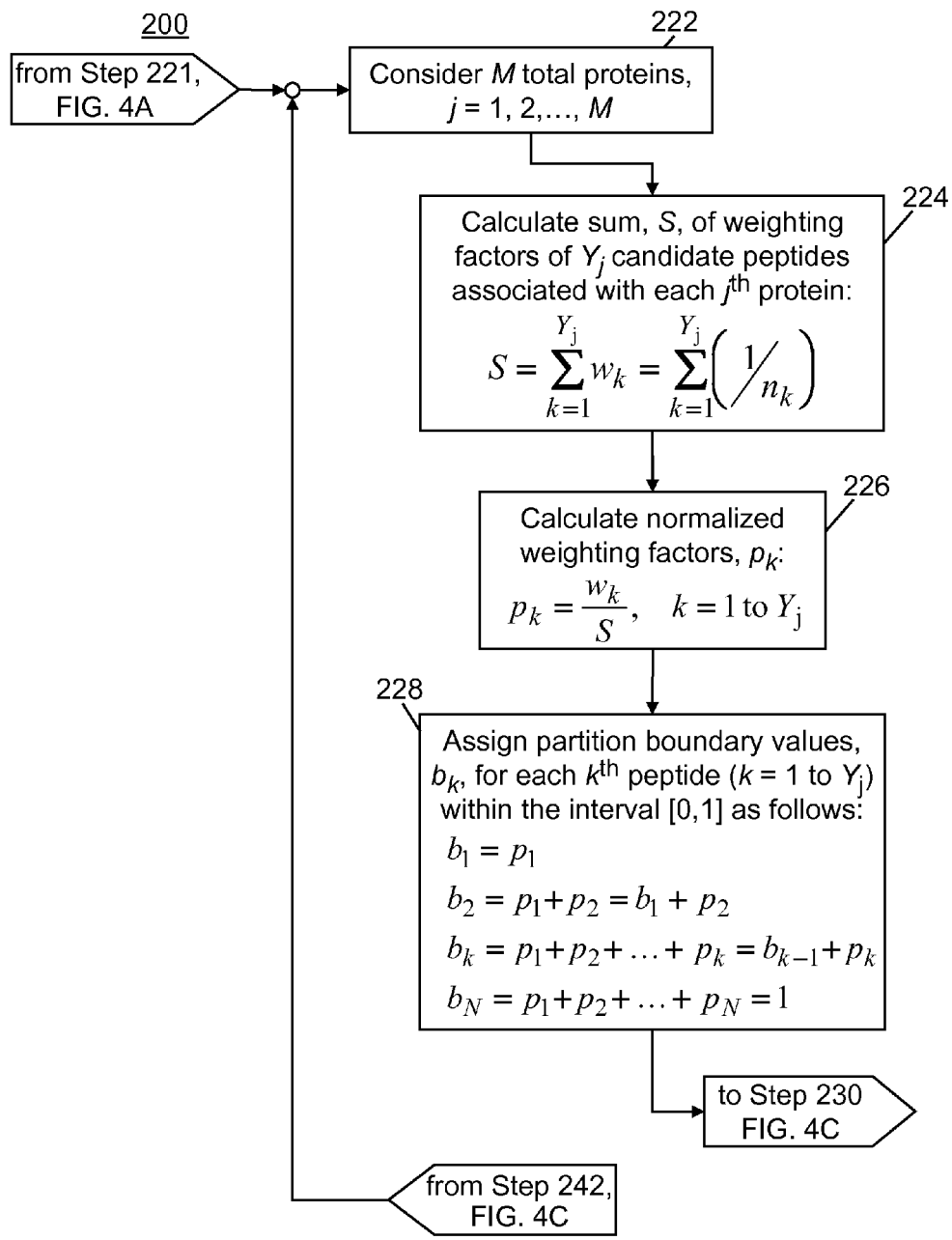
Figure 4C:
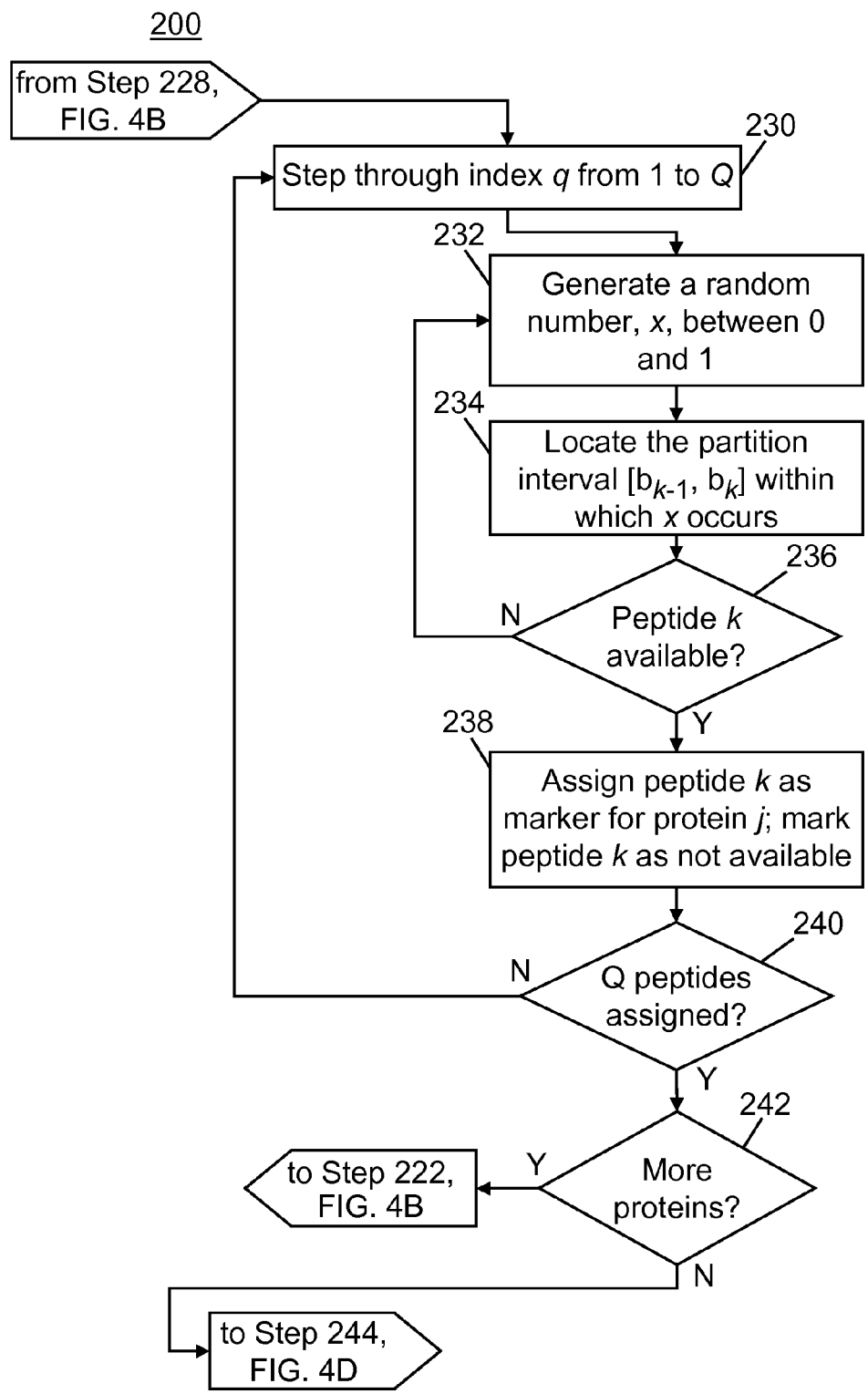
Figure 4D:
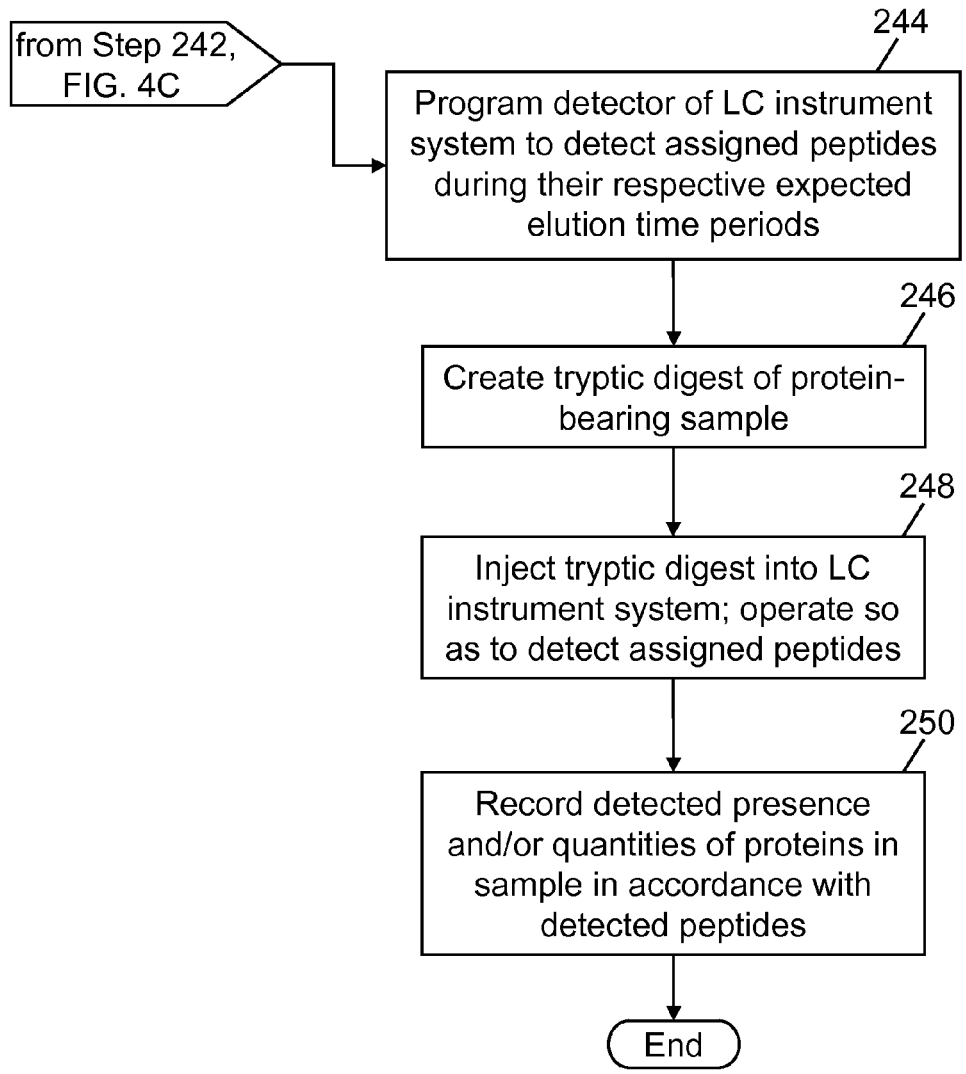

Recently, peptide retention time prediction models, such as those based on hydrophobicity index, have been extended so as to take into account not only amino acid composition but also residue position within the peptide chain [e.g., Krokhin et al., "*An Improved Model for Prediction of Retention Times of Tryptic Peptides in Ion Pair Reversed-phase HPLC*" Molecular & Cellular Proteomics: MCP, 2004, 3(9), pp. 908-919; Krokhin, "*Sequence-specific retention calculator. Algorithm for peptide retention prediction in ion-pair RP-HPLC: application to* 300- *and* 100-*A pore size C18 sorbents*", Anal Chem., 2006, 78(22), pp. 7785-7795; Krokhin et al. "*Use of Peptide Retention Time Prediction for Protein Identification by off-line Reversed-Phase HPLC-MALDI MS/MS*", Anal. Chem., 2006, 78(17), pp 6265-6269; Spicer et al., "*Sequence-Specific Retention Calculator. A Family of Peptide Retention Time Prediction Algorithms in Reversed-Phase HPLC: Applicability to Various Chromatographic Conditions and Columns*", Anal. Chem., 2007, 79(22), pp 8762-8768; Dwivedi et al., "*Practical Implementation of 2D HPLC Scheme with Accurate Peptide Retention Prediction in Both Dimensions for High-Throughput Bottom-Up Proteomics*", Anal. Chem., 2008, 80(18), pp 7036-7042; Krokhin and Spicer, "*Peptide Retention Standards and Hydrophobicity Indexes in Reversed-Phase High-Performance Liquid Chromatography of Peptides*", Anal. Chem., 2009, 81(22), pp 9522-9530]. To account for the LC-system dependence, calibration mixtures are available that contain a chosen set of peptide compounds. Once a calibration is available, then the measured retention time (R.T.) of test peptides tends to closely follow the predicted R.T., which is generated based on both the applied calibration as well as the predictions of the sequence-specific retention time calculator algorithm (FIG. 3).

Once the list of retention times has been calculated for all expected peptides of the theoretical tryptic digest, the various peptides are sorted in order of retention time (step 214). In the loop of steps 216-221, a calculation is made, for each peptide, how many other peptides in the set have a scheduling overlap (step 218), where a "scheduling overlap" is defined as the condition where the predicted retention time difference between the peptide under consideration and another of the peptides is less than the scheduling window, e.g. the chromatographic peak width or an otherwise predetermined measurement time duration. Thus, in step 216, the peptides are considered in order of their retention time. For each peptide, the method performs the overlap calculation (step 218) by first moving backward in the list counting all the peptides encountered at earlier retention times until either the beginning of the list is reached or up to one scheduling window backward in time from the R.T of the peptide under consideration. The count is continued similarly moving forward until either the end of the list is reached or up to one scheduling window forward from the R.T of the peptide under consideration. The cumulative overlap count—both forward and backward—is then recorded for each peptide.

In step 220, the multiplicative inverse of the overlap count as the weighting factor for adjusting the probability of selecting each peptide. Then, using these weighting factors, a certain predetermined number, Q, of diagnostic peptides are determined for each of the M proteins of interest, in accordance with the present teachings, such that the aggregate distribution of retention times will, on average, will minimize the extent of scheduling conflicts. This peptide selection is performed in the loop of steps 222-240 which spans FIGS. 4B and 4C. The number Q can be set to any desired value such as Q=3. As each protein j is considered, the master list of theoretical peptides (i.e., see step 206) is consulted such that only those peptides that are predicted to be generated in the digestion of protein j are considered. Suppose there are a total of Y of such candidate peptides. Considering all and only these $Y_j$ candidate peptides associated with the particular protein (protein j) under consideration, the real-number interval [0,1] is then partitioned (conceptually) among the candidate peptides. The partitions are made of unequal size in accordance with the various weighting factors. To calculate the size of each partition, a sum of the weighting factors is calculated in step 224 where each weighting factor, $w_k$, is equal to $1/n_k$, where $n_k$ is the number of overlaps encountered by peptide k. Suppose this sum is S. Then, in step 226, the partition sizes are normalized to values $p_k = (w_k/S)$ so that the partition sizes, $p_k$, sum to unity. Next (step 228) the boundary values of the various partitions are calculated. For example, let $b_k$ denote the sum of the first k normalized partition sizes. Then, the partition of the interval [0,1] that belongs to the candidate peptide k is the interval $[b_{k-1}, b_k]$. The values $b_1 \ldots b_N$ can be thought of as the positions of partition boundaries within the interval [0,1].

Still considering each protein (protein j) under consideration, steps 230-240 randomly select a total of Q peptides (for example 3 peptides) from among the $Y_j$ candidate peptides using the above weighting scheme. This is performed by generating a uniformly random number, x, in the interval [0,1] (step 232) and then determining (step 234) which interval $[b_{k-1}, b_k]$ within which the random number, x, occurs. The peptide k is then selected for association with the protein j (step 238) unless this peptide has already been selected. If the peptide has already been selected, then steps 232-236 are executed again. If peptide k has not yet been selected, then peptide k is added to a list of selected peptides. Steps 230-240 are repeatedly executed until Q diagnostic peptides have been associated with the protein j. Steps 222-242 are executed for each protein of interest until all such proteins have been considered.

After all proteins of interest have been associated with diagnostic peptides, then, in step 244, an LC instrument system—comprising a liquid chromatograph as well as a detector or detection system coupled to the chromotograph so as to detect analytes eluting from the chromatograph—is programmed so to automatically attempt to detect all of the assigned peptides (as determined during the previous steps of the method 200) during their respective expected elution time periods. (The phrase "attempt to detect" is used here because not all proteins of interest may be present in a sample.) In principle, any type of detector may be employed. Preferably, however, the detector comprises a mass spectrometer because of the high sensitivity and analytical specificity of mass spectrometer instruments.

If the detector is a mass spectrometer, then the programming step (step 244) will generally include selecting, for each peptide, a diagnostic ion or ions to be searched for so as to recognize the presence of the peptide and possibly to quantify the peptide. In this case, the programming of the mass spectrometer detector may include programmed instructions to automatically search for a precursor ion and, if the precursor ion is recognized, programmed instructions to fragment the precursor ion and to search for specific product ions formed during the fragmentation. Because a mass spectrometer can perform this sequence of steps in a time period that is much shorter than a typical elution time period of any peptide, the mass spectrometer can successfully detect multiple peptide analytes essentially simultaneously in the case of a small or moderate number of overlapping peptide elution peaks. However, there is an upper limit to how many co-eluting peptides can be simultaneously measured. The methods in accordance with the present teachings are designed to prevent this upper limit from being reached, in most instances.

In step 246, a tryptic digest is made of a protein-bearing sample of interest. In principle, this step will physically generate the same peptide species as predicted in step 204 for any of the proteins of interest that are actually present in the sample. In step 248, the tryptic digest in introduced into the LC instrument system which is then operated, in accordance with the instructions programmed in step 244 so as to detect any of the assigned peptides that might be present in the tryptic digest. Finally, in step 250 the detected presence and/or quantities of proteins in the sample is recorded as inferred from the detected peptides, if any.

Figure 5A:
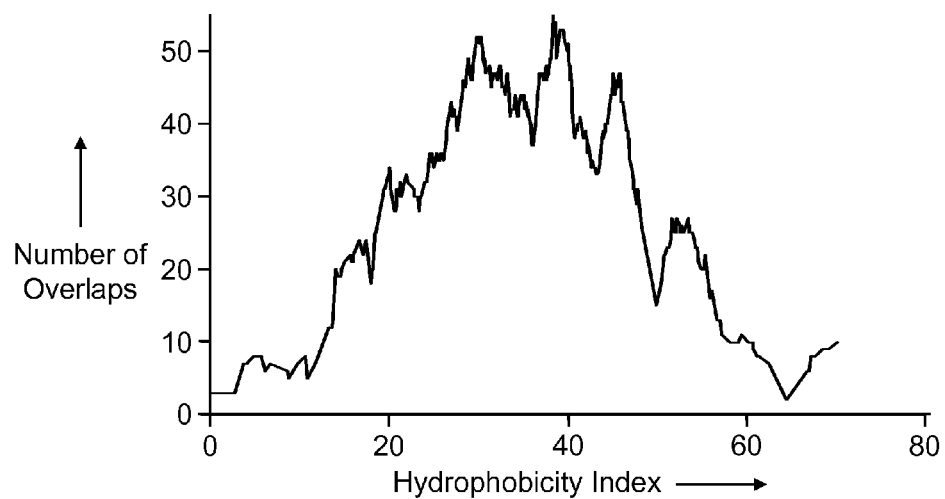
FIG. 5A is a graphical depiction of the number of peptide elution overlaps that are predicted to occur for each peptide within a group of 433 randomly selected peptides, plotted versus hydrophobicity index.
Figure 5B:
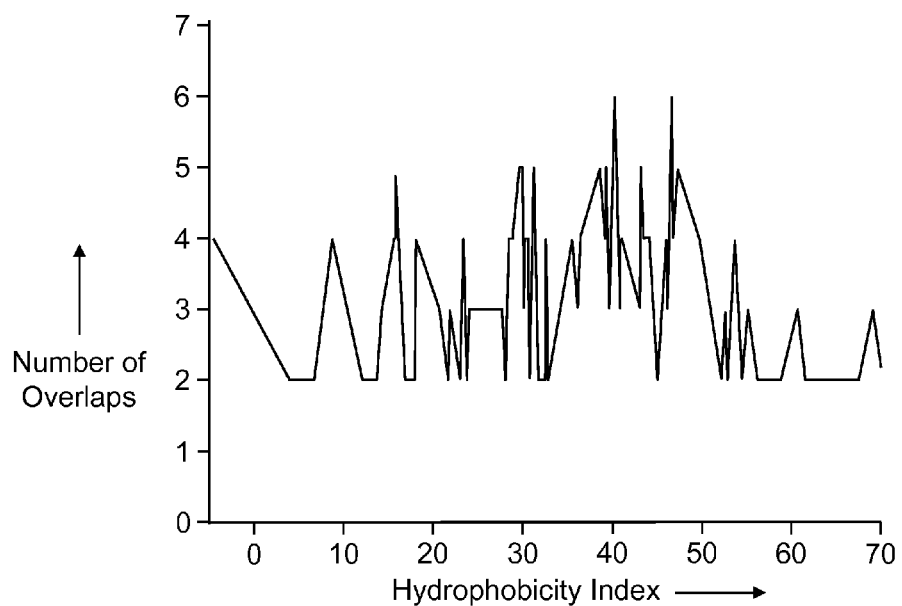
FIG. 5B is a graphical depiction of the number of peptide elution overlaps that are predicted to occur over the course of elution of each one of a subset of 145 peptides selected in accordance with the methods of the present teachings.

FIG. 5A-5B are simulated plots of the number of peptide elution overlaps predicted to occur when peptides are selected for detection by two different methods. FIG. 5A is a graphical depiction of the number of peptide elution overlaps that are predicted to occur for each peptide within a group of 433 randomly selected peptides. The number of elution overlaps is plotted versus hydrophobicity index which, for purposes of this example, may serve as a proxy for retention time. FIG. 5A indicates that when peptides are selected randomly for detection, as in conventional methods, a large number of such peptides may elute simultaneously. The simultaneous elution of a large number of peptides may stress the ability of a mass spectrometer instrument to successfully complete a survey for the presence of all required peptides. By contrast, FIG. 5B is a graphical depiction of the number of peptide elution overlaps that are predicted to occur over the course of elution of each one of a subset of 145 peptides, where the peptides are selected and scheduled for detection in accordance with the methods of the present teachings. In this latter case, the number of elution overlaps is roughly uniform—at a relatively low number of such overlaps—over the course of an entire proteomic analysis.

The discussion included in this application is intended to serve as a basic description. Although the invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the scope and essence of the invention. As but one example, although the present examples have described the use of mass spectrometry for detection, other means of chemical detection may be employed such as molecular vibrational spectroscopy (e.g., Raman spectroscopy, resonance Raman spectroscopy, surface-enhanced Raman spectroscopy) or UV-visible spectroscopy. The detection techniques may be employed to detect the presence of unmodified analytes or, alternatively, may be employed to detect reporter molecular groups—such as isotopically labeled groups or fluorophore labeled groups—that have been chemically bound to proteins prior to digestion and chromatographic analysis. As another example, although the description herein has described the analysis of peptides for the purposes of recognizing or quantifying proteins, the same methods may be employed to recognize or quantify biopolymers of other classes if: (a) each biopolymer of interest may be chemically fragmented or reacted so as to produce polymer fragments (e.g., oligomers) or other product species whose detected presence can be used to infer the information about the presence or quantity of the parent biopolymer in a sample; (b) the type of fragments or product species can be theoretically predicted for each biopolymer of interest; and (c) the chromatographic separation times—such as elution times or retention times—of the various theoretically predicted fragments or product species can be predicted or estimated. Neither the description nor the terminology is intended to limit the scope of the invention. Any patents, patent applications, patent application publications or other literature mentioned herein are hereby incorporated by reference herein in their respective entirety as if fully set forth herein.

What is claimed is:

1. A method for detecting, within a sample, the presence or quantity of each of two or more biopolymer molecules of a list of known biopolymer molecules, comprising:
    calculating, for each biopolymer molecule, a respective list of oligomer molecules predicted to be produced by a chemical reaction or processing of the respective biopolymer molecule;
    calculating a respective predicted chromatographic elution time period for each unique oligomer molecule of the set of lists of oligomer molecules, said predicted chromatographic elution time periods encompassing a finite retention time period over which a value of a number of co-eluting oligomer molecules is variable with time;
    calculating, for each unique oligomer molecule, a respective weighted oligomer selection probability, wherein a respective weighting factor assigned to each said oligomer molecule is calculated, in part, as an inverse of a respective number of other of said unique oligomer molecules for which elution times are predicted to overlap with the elution of said each oligomer molecule, based on the predicted chromatographic elution time periods;
    for each biopolymer molecule, assigning one or more unique oligomer molecules selected from the respective list of oligomer molecules as a proxy for the respective biopolymer molecule, wherein the assigning is performed using the set of weighted oligomer selection probabilities;
    scheduling a plurality of oligomer detection events of a detection system, wherein each oligomer detection event corresponds to a respective one of the predicted chromatographic elution time periods of the assigned oligomer molecules;
    performing the chemical reaction or processing of the sample so as to generate a processed sample;
    introducing the processed sample into a chromatographic system such that oligomers eluting from the chromatographic system, if any, are introduced into the detection system; and
    operating the detection system so as to search for the presence or quantity of each of the assigned oligomer molecules over the finite retention time period in accordance with the plurality of scheduled oligomer detection events.

2. A method as recited in claim 1, wherein the operating of the detection system comprises operating a mass spectrometer detection system, such that specific ions generated from each assigned oligomer molecule may be detected.

3. A method as recited in claim 1, wherein the biopolymer molecules are proteins, the oligomer molecules are peptides, wherein the performing of the chemical reaction or processing of the sample comprises performing a tryptic digest of the proteins, and wherein the operating of the detection system comprises operating a mass spectrometer detection system, such that specific ions generated from each assigned peptide molecule may be detected.

4. A method as recited in claim 3, wherein the calculating of a respective predicted chromatographic elution time period for each unique oligomer molecule of the set of lists of oligomer molecules comprises calculating a respective chromatographic elution time period for each peptide, wherein the calculating is based on hydrophobicity indices of the peptides.

5. A method as recited in claim 3, wherein the calculating of a respective predicted chromatographic elution time period for each unique oligomer molecule of the set of lists of oligomer molecules comprises calculating a respective chromatographic elution time period for each peptide, wherein the calculating is based on compositions and amino acid sequences of the peptides.

6. A method as recited in claim 3, wherein the operating of the detection system so as to search for the presence or quantity of each of the assigned oligomer molecules comprises operating the mass spectrometer system so as to perform, during each scheduled oligomer detection event, the steps of:
attempting to detect ions comprising a specific mass-to-charge (m/z) ratio that is characteristic of the presence of a respective assigned peptide associated with the scheduled detection event; and,
if said ions are detected:
fragmenting a portion of the detected ions so as to form product ions; and
attempting to detect product ions comprising a specific different ink ratio that is diagnostic of the presence of a respective assigned peptide associated with the scheduled detection event.

7. A method for detecting, within a sample, the presence or quantity of each of two or more biopolymer molecules of a list of known biopolymer molecules, comprising:
calculating, for each biopolymer molecule, a respective list of oligomer molecules predicted to be produced by a chemical reaction or processing of the respective biopolymer molecule;
calculating a respective predicted chromatographic elution time period for each unique oligomer molecule of the set of lists of oligomer molecules, said predicted chromatographic elution time periods encompassing a finite retention time period over which a value of a number of oligomer molecules that elute per unit time is variable with time;
dividing the finite retention time period into a plurality of equal-width time bins;
calculating, for each unique oligomer molecule, a respective weighted oligomer selection probability, wherein a respective weighting factor assigned to each said oligomer molecule is calculated, in part, as an inverse of a respective number of other of said unique oligomer molecules that are predicted, based on the predicted chromatographic elution time periods, to elute within the same time bin as the elution of said each oligomer molecule;
for each biopolymer molecule, assigning one or more unique oligomer molecules selected from the respective list of oligomer molecules as a proxy for the respective biopolymer molecule, wherein the assigning is performed using the set of weighted oligomer selection probabilities;
scheduling a plurality of oligomer detection events of a detection system, wherein each oligomer detection event corresponds to a respective one of the predicted chromatographic elution time periods of the assigned oligomer molecules;
performing the chemical reaction or processing of the sample so as to generate a processed sample;
introducing the processed sample into a chromatographic system such that oligomers eluting from the chromatographic system, if any, are introduced into the detection system; and
operating the detection system so as to search for the presence or quantity of each of the assigned oligomer molecules over the finite retention time period in accordance with the plurality of scheduled oligomer detection events.

8. A method as recited in claim 7, wherein the operating of the detection system comprises operating a mass spectrometer detection system, such that specific ions generated from each assigned oligomer molecule may be detected.

9. A method as recited in claim 7, wherein the biopolymer molecules are proteins, the oligomer molecules are peptides, wherein the performing of the chemical reaction or processing of the sample comprises performing a tryptic digest of the proteins, and wherein the operating of the detection system comprises operating a mass spectrometer detection system, such that specific ions generated from each assigned peptide molecule may be detected.

10. A method as recited in claim 9, wherein the calculating of a respective predicted chromatographic elution time period for each unique oligomer molecule of the set of lists of oligomer molecules comprises calculating a respective chromatographic elution time period for each peptide, wherein the calculating is based on hydrophobicity indices of the peptides.

11. A method as recited in claim 9, wherein the calculating of a respective predicted chromatographic elution time period for each unique oligomer molecule of the set of lists of oligomer molecules comprises calculating a respective chromatographic elution time period for each peptide, wherein the calculating is based on compositions and amino acid sequences of the peptides.

12. A method as recited in claim 9, wherein the operating of the detection system so as to search for the presence or quantity of each of the assigned oligomer molecules comprises operating the mass spectrometer system so as to perform, during each scheduled oligomer detection event, the steps of:
attempting to detect ions comprising a specific mass-to-charge (m/z) ratio that is characteristic of the presence of a respective assigned peptide associated with the scheduled detection event; and,
if said ions are detected:
fragmenting a portion of the detected ions so as to form product ions; and
attempting to detect product ions comprising a specific different m/z ratio that is diagnostic of the presence of a respective assigned peptide associated with the scheduled detection event.

13. A method for detecting, within a sample, the presence or quantity of each of two or more biopolymer molecules of a list of known biopolymer molecules, comprising:
calculating, for each biopolymer molecule, a respective list of oligomer molecules predicted to be produced by a chemical reaction or processing of the respective biopolymer molecule;

calculating a respective predicted chromatographic elution time period for each unique oligomer molecule of the set of lists of oligomer molecules, said predicted chromatographic elution time periods encompassing a finite retention time period over which a value of a number of oligomer molecules that elute per unit time is variable with time;

calculating, from the predicted chromatographic elution time periods, a continuous model curve that approximates the number of oligomer molecules that elute per unit time over the finite retention time period;

calculating, for each unique oligomer molecule, a respective weighted oligomer selection probability, wherein a respective weighting factor assigned to each said oligomer molecule is calculated, in part, as an inverse of the model curve evaluated at the respective elution time of said each oligomer molecule;

for each biopolymer molecule, assigning one or more unique oligomer molecules selected from the respective list of oligomer molecules as a proxy for the respective biopolymer molecule, wherein the assigning is performed using the set of weighted oligomer selection probabilities;

scheduling a plurality of oligomer detection events of a detection system, wherein each oligomer detection event corresponds to a respective one of the predicted chromatographic elution time periods of the assigned oligomer molecules;

performing the chemical reaction or processing of the sample so as to generate a processed sample;

introducing the processed sample into a chromatographic system such that oligomers eluting from the chromatographic system, if any, are introduced into the detection system; and operating the detection system so as to search for the presence or quantity of each of the assigned oligomer molecules over the finite retention time period in accordance with the plurality of scheduled oligomer detection events.

14. A method as recited in claim 13, wherein the operating of the detection system comprises operating a mass spectrometer detection system, such that specific ions generated from each assigned oligomer molecule may be detected.

15. A method as recited in claim 13, wherein the biopolymer molecules are proteins, the oligomer molecules are peptides, wherein the performing of the chemical reaction or processing of the sample comprises performing a tryptic digest of the proteins, and wherein the operating of the detection system comprises operating a mass spectrometer detection system, such that specific ions generated from each assigned peptide molecule may be detected.

16. A method as recited in claim 15, wherein the calculating of a respective predicted chromatographic elution time period for each unique oligomer molecule of the set of lists of oligomer molecules comprises calculating a respective chromatographic elution time period for each peptide, wherein the calculating is based on hydrophobicity indices of the peptides.

17. A method as recited in claim 15, wherein the calculating of a respective predicted chromatographic elution time period for each unique oligomer molecule of the set of lists of oligomer molecules comprises calculating a respective chromatographic elution time period for each peptide, wherein the calculating is based on compositions and amino acid sequences of the peptides.

18. A method as recited in claim 15, wherein the operating of the detection system so as to search for the presence or quantity of each of the assigned oligomer molecules comprises operating the mass spectrometer system so as to perform, during each scheduled oligomer detection event, the steps of:

attempting to detect ions comprising a specific mass-to-charge (m/z) ratio that is characteristic of the presence of a respective assigned peptide associated with the scheduled detection event; and, if said ions are detected:

fragmenting a portion of the detected ions so as to form product ions; and attempting to detect product ions comprising a specific different m/z ratio that is diagnostic of the presence of a respective assigned peptide associated with the scheduled detection event.

19. A method as recited in claim 13, wherein the assigning of the one or more oligomer molecules uses a set of weighted selection probabilities chosen such that a selection probability weighting factor progressively increases away from a mean oligomer molecule elution time determined from the model curve.

* * * * *